United States Patent
Bryner (10) Patent No.: US 8,658,548 B2
(45) Date of Patent: Feb. 25, 2014

(54) EXTREMELY HIGH LIQUID BARRIER FABRICS

(75) Inventor: Michael Allen Bryner, Midlothian, VA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 26 days.

(21) Appl. No.: 13/072,870

(22) Filed: Mar. 28, 2011

(65) Prior Publication Data

US 2011/0177741 A1 Jul. 21, 2011

Related U.S. Application Data

(63) Continuation of application No. 12/538,303, filed on Aug. 10, 2009, now abandoned.

(51) Int. Cl.
*B32B 5/26* (2006.01)

(52) U.S. Cl.
USPC ............... 442/346; 442/79; 442/82; 442/334; 442/340; 442/351; 442/381; 442/382; 442/400; 442/401

(58) Field of Classification Search
USPC ............. 442/79, 82, 381, 382, 400, 401, 334, 442/340, 346, 351
See application file for complete search history.

(56) References Cited

U.S. PATENT DOCUMENTS

| | | | |
|---|---|---|---|
| 4,011,067 A | 3/1977 | Carey, Jr. | |
| 4,044,404 A | 8/1977 | Martin et al. | |
| 4,069,026 A | 1/1978 | Simm et al. | |
| 4,127,706 A | 11/1978 | Martin et al. | |
| 4,524,036 A | 6/1985 | Gilding et al. | |
| 4,632,873 A | 12/1986 | Mizuno et al. | |
| 5,484,645 A | 1/1996 | Lickfield et al. | |
| 5,522,879 A | 6/1996 | Scopelianos | |
| 5,679,379 A | 10/1997 | Fabbricante et al. | |
| 5,695,849 A * | 12/1997 | Shawver et al. | 428/131 |
| 5,885,909 A | 3/1999 | Rudisill et al. | |
| 6,106,913 A | 8/2000 | Scardino et al. | |
| 6,110,590 A | 8/2000 | Zarkoob et al. | |
| 6,114,017 A | 9/2000 | Fabbricante et al. | |
| 6,139,941 A * | 10/2000 | Jankevics et al. | 428/195.1 |
| 6,183,670 B1 | 2/2001 | Torobin et al. | |
| 6,187,696 B1 | 2/2001 | Lim et al. | |
| 6,265,333 B1 | 7/2001 | Dzenis et al. | |
| 6,269,513 B1 | 8/2001 | Torobin | |
| 6,315,806 B1 | 11/2001 | Torobin et al. | |
| 6,395,046 B1 | 5/2002 | Emig et al. | |

(Continued)

FOREIGN PATENT DOCUMENTS

| | | |
|---|---|---|
| CA | 2305004 | 10/2000 |
| EP | 1 364 773 A1 | 11/2003 |

(Continued)

OTHER PUBLICATIONS

W. John G. Mc Gulloch, Ultrafine to Nanofine Fibers Via Spunmelt Processes, Nonwoven World, 2000, pp. 87-92, August-September.

(Continued)

*Primary Examiner* — Andrew Piziali (57) ABSTRACT

One embodiment of the present invention is a nonwoven fabric comprising a support web and a fibrous barrier web, having a hydrohead of at least about 145 cm and a Frazier permeability of at least about 0.3 $m^3/m^2$-min.

15 Claims, 7 Drawing Sheets

(56) References Cited

U.S. PATENT DOCUMENTS

| | | | |
|---|---|---|---|
| 6,520,425 | B1 | 2/2003 | Reneker |
| 6,613,268 | B2 | 9/2003 | Haynes et al. |
| 6,723,669 | B1* | 4/2004 | Clark et al. .................. 442/347 |
| 2002/0046656 | A1* | 4/2002 | Benson et al. .................. 95/287 |
| 2002/0117782 | A1 | 8/2002 | Haynes et al. |
| 2003/0106294 | A1 | 6/2003 | Chung et al. |
| 2003/0129909 | A1 | 7/2003 | Zucker |
| 2003/0177909 | A1 | 9/2003 | Koslow |

FOREIGN PATENT DOCUMENTS

| | | |
|---|---|---|
| GB | 1 527 592 | 10/1978 |
| GB | 2 104 087 A | 3/1983 |
| KR | 2002-0093178 | 12/2002 |
| KR | 2002-0093179 | 12/2002 |
| WO | WO 99/18893 A1 | 4/1999 |
| WO | WO 00/22207 A2 | 4/2000 |
| WO | WO 00/22207 A3 | 4/2000 |
| WO | WO 00/37723 A | 6/2000 |
| WO | WO 01/09425 A | 2/2001 |
| WO | WO 01/26610 A1 | 4/2001 |
| WO | WO 01/27365 A1 | 4/2001 |
| WO | WO 02/20136 A | 3/2002 |
| WO | WO 02/20668 A2 | 3/2002 |
| WO | WO 02/20668 A3 | 3/2002 |
| WO | WO 02/43951 A2 | 6/2002 |
| WO | WO 03/080905 A1 | 10/2003 |
| WO | WO 2004/026055 A2 | 4/2004 |
| WO | WO 2004/026167 A2 | 4/2004 |
| WO | WO 2004/027135 A2 | 4/2004 |

OTHER PUBLICATIONS

Stanley E. Ross, Electrospinning: The Quest for Nanofibers, Fiber Engeering, International Fiber Journal, Oct. 2001, pp. 50-53.

Dr. Heidi Schreuder-Gibson (Bill Smith), US Army develops fabric membrane to provide multipurpose protection, Technical Textiles Internationsl, May 1998, p. 6.

Phillip Gibson, Heidi Schreuder-Gibson and Christopher Pentheny, Electrospinning Technology: Direct Application of Tailorable Ultrathin Membrances, Journal of Coated Fabrics, Jul. 1998, pp. 63-72, vol. 28, Technomic Publishing Co., Inc.

Jayesh Doshi, Advancing Techniques in Electrospinning Fibers, Section 12, Nanofiber based Nonwoven Composites, Its Properties, and Applications, Forbes, Jul. 23, 2001 Issue, Red Herring, Jul. 17, 2001 Issue, Chemical & Engineering News, Oct. 16, 2000 Issue.

Michel M. Bergshoef and G. Julius Vancso, Transparent Nanocomposites with Ultrathin, Electrospun Nylon-4,G Fiber Reinforcement, Advanced Materials, 1999, pp. 1362-1365, 11 No. 16, Wiley-VCH Verlag GmbH, Weinheim.

A. Buer, S. C. Ugbolue, and S. B, Warner, Electrospinning and Properties of Some Nanotibers, Textile Research Journal, 2001, pp. 323-328, 71(4).

Y, A. Dzenis and D. H. Reneker, Polymer Hybrid Nano/Micro Composites, Proceedings of the American Society for Composites, Ninth Technical Conference, Sep. 1994, pp. 657-665, Technomic Publishing Co. Inc. Lancaster-Basel.

Jong-Sang Kim and Darrell H. Reneker, Polybenzimidazole Nanofiber Produced by Electrospinning, Polymer Engineering and Science, May 1999, pp. 849-854, vol. 39, No. 5.

Darrell H. Reneker and IKS00 Chun, Nanometre diameter fibres of polymer, produced by electrospinning, Nanotechnology, 1996, pp. 216-223, 7, IOP Publishing Ltd., Printed in UK.

Peter K. Baumgarten, Electrostatic Spinning of Acrylic Mlcrofibers, Journal of Colloid and interface Science, May 1971, pp. 71-79, vol. 36, No. 1.

A, E. Zachariades, R. S. Porter, Jayesh Doshi, Gokol Srinivasan, and Darrell H. Reneker, High Modulus Polymers, A Novel Electrospinning Process, Polymer News, 1995, pp. 206-207, vol. 20, Overseas Publishers Association, Amsterdam B.V., Pubblished under License by Gordon and Breach Science Publishers SA.

Raimund Jaeger, Michel M. Bergshoef, Cristina Martin I Batlle, Holger Schonherr, G. Julius Vancso, Electrospinning of Ultra-Thin Polymer Fibers, Macromol. Symp. 1998, pp. 141-150, vol. 127, Huthig & Wepf Verlag. Zug.

H. Fong, I. Chun, D. H. Reneker, Beaded nanofibers formed during eletrospinning, Polymer.. 1999, pp. 4606-4592, 40, Elsevier Science Ltd.

Shahrzad Zarkoob, Darrell H. Reneker, R. K. Eby, Steven D. Hudson, Dale Ertley, Wade W. Adams, Structure and Morphology of Nano Electrospun Silk Fibers, Polymer Preprints, 1998, pp. 244-245, vol. 39, Issue 2.

X. Fang and D. H. Reneker, DNA Fibers by Electrospinning, J. Macromol. Sci.-Phys., 1997, pp. 169-173, B36(2), Marcel Dekker, Inc.

Gokul Srinivasan and Darrell H. Renekert, Structure and Morphology of Small Diameter Electrospun Aramid Fibers, Polymer International, 1995, pp. 195-201, 36, SCI, Great Britain.

Fang, Xiaoyan, Application of electrospinning for polymers, Dissertation Abstracts International, Feb. 1998, p, 4246-B, vol. 58 No. 8.

Jayesh Doshi and Darrell H. Reneker, Electrospinning Process and Applications of Electrospun Fibers, Journal of Electrostatics, 1995, 151-100, 35, Elsevier Science B.V.

Dr. Heidi Schreuder-Gibson, US Army Universities Team Up to Develop Electrospun Nanofibers for Clothing Applications, International Fiber Journal, 1998, pp. 49-50, vol. 13.

Phillip Gibson, Donald Rivin, Cyrus Kendrick, and Heidi Schreuder-Gibson, Humidity-Dependent Air Permeability of Textile Materials, Textile Research Journal, 1999, pp. 311-317, 69(5).

Kristine Graham, Ming Ouyant, Tom Raether, Tim Grafe, Bruce McDonald, Paul Knauf, Polymeric Nanofihers in Air Filtration Applications, Presented at the Fifteenth Annual Technical Conference & Expo of the American Filtration & Separations Society, Apr. 9-12, 2002, © 2002 Donaldson Company Inc.

* cited by examiner

EXTREMELY HIGH LIQUID BARRIER FABRICS

PRIORITY INFORMATION

This application is a continuation of, and claims priority to, U.S. application Ser. No. 12/538,303, filed on Aug. 10, 2009 and now abandoned.

BACKGROUND

This invention relates to nonwoven fibrous structures and more particularly to breathable fabrics and sheet structures formed by fibers which are held together without weaving or knitting.

Nonwoven fibrous structures have existed for many years and today there are a number of different nonwoven technologies in commercial use. To illustrate the breadth of nonwoven technologies, paper is probably one of the earliest developed nonwoven fibrous structures. Nonwoven technologies continue to be developed by those seeking new applications and competitive advantages. One broad market area that has proven to be highly desirable because of its large volume and economics is the protective apparel market. This market comprises protection from hazardous chemicals such as in chemical spill clean up, from liquids such as blood in the medical field and from dry particulates or other hazards such as painting or asbestos removal.

It is known that for a garment to be comfortable, it must accommodate the body's physiological need for thermal regulation. In warm environments, heat energy must be expelled from the body. This is done principally by a combination of direct thermal conduction of heat away from the body through the fabric and air layers at the skin surface, convection of heat away from the body by flowing air, and by the cooling effects of evaporation of sweat from the surface of the skin. Clothing which appreciably inhibits heat transfer can cause heat and moisture buildup and this can result in discomfort due to warm, sticky, clammy and or sweaty sensations. In the extreme case, for example, where protective clothing prevents adequate thermal regulation during activity in a warm and humid environment, such clothing limitations not only lead to discomfort, but can result in life-threatening heat stress. For this reason, frequently, clothing limitations impose limitations on activity to avoid the consequences of heat stress.

Studies have shown that the most comfortable garments with the least restrictions on physical activity in warm, humid environments, are those most able to breathe through mechanisms of air exchange with the environment. (Bernard, T. E., N. W. Gonzales, N. L. Carroll, M. A. Bryner and J. P. Zeigler. "Sustained work rate for five clothing ensembles and the relationship to air permeability and moisture vapor transmission rate." American Industrial Hygiene Conference, Toronto, June 1999; N. W. Gonzales, "Maximum Sustainable Work for Five Protective Clothing Ensembles and the Effects of Moisture Vapor Transmission Rates and Air Permeability" Master's Thesis, College of Public Health, University of South Florida, December 1998).

Physical activity flexes fabric and garment. If a fabric has low enough resistance to air flow, this, in turn, produces a pumping action which pushes and pulls air back and forth through the fabric. By this mechanism, the exchange of warm moisture laden air within the garment with ambient air provides a significant cooling effect. Tests of protective garments made of the same cut, but with widely differing air flow resistance under warm humid conditions (32° C., 60% RH), have shown that the garments made of fabrics with the least air flow resistance repeatedly allowed subjects to achieve higher levels of activity without incurring heat stress. Conversely, garments made of fabrics with the highest air flow resistance limited the physical activity of the same subjects to the lowest levels to avoid heat stress. Garments made of fabrics having intermediate air flow resistance allowed subjects to achieve intermediate levels of activity without heat stress. The intermediate activity levels correlated very well with the air flow resistance of the fabric.

Clearly, under conditions where the body must transfer heat and moisture to maintain comfort or avoid heat stress, it is desirable to for garments to be made with fabrics having low air flow resistance.

Clothing provides protection from hazards in the environment. The degree of protection clothing imparts is dependent upon the effectiveness of the barrier characteristics of the clothing. Where the function of the barrier is to keep environmental particulates or fluids from penetrating a garment to reach the wearer, barrier is easily correlated with fabric pore size. The most effective barriers generally have the smallest pore size.

Unfortunately, smaller pore size also generally results in higher air flow resistance. In the studies cited above, the garments with the highest barrier properties had the lowest airflow permeability and vise versa. So the ability to provide effective barrier protection in clothing and the ability to provide low air flow resistance, i.e., high air flow permeability, in the same garment are inversely related.

Hydrostatic head or "hydrohead" (AATCC TM 127-194) is a convenient measure of the ability of a fabric to prevent water penetration. It is presented as the pressure, in centimeters of water column (cmwc) required to force liquid water through a hydrophobic fabric. It is known that hydrohead depends inversely on pore size. Lower pore size produces higher hydrohead and higher pore size produces lower hydrohead.

Fabric air flow permeability is commonly measured using the Frazier measurement (ASTM D737). In this measurement, a pressure difference of 124.5 N/m$^2$ (0.5 inches of water column) is applied to a suitably clamped fabric sample and the resultant air flow rate is measured as Frazier permeability or more simply as "Frazier". Herein, Frazier permeability is reported in units of m$^3$/m$^2$-min. High Frazier, corresponds to high air flow permeability and low air flow resistance while low Frazier corresponds to low air flow permeability and high air flow resistance.

Microporous films have been used in barrier materials to achieve extremely high hydrostatic head liquid barrier properties, but at the expense of breathability, such that their Frazier permeabilities are unacceptably low, rendering fabrics containing such films uncomfortable for the wearer.

Currently, most melt-spun fibers have diameters on the order of several tens of micrometers, whereas melt-blown fibers are known to have fiber diameters on the order of from about 1 to 10 micrometers. Recently, many researchers have made efforts to decrease fiber sizes in order to obtain different benefits, as compared to conventional fibers.

Advances have been made in providing both high hydrohead properties and high Frazier properties in the same fabric. For example, U.S. Pat. No. 5,885,909 discloses low or sub-denier nonwoven fibrous structures which demonstrate an unusual combination of high Frazier permeability and high hydrostatic head liquid barrier properties.

More recently, efforts have centered around obtaining fiber diameters in the 'nanofiber' range, i.e. with diameters on the order of less than about 0.5 micrometers (500 nm). However, production of such small fibers has presented many problems including low throughput, poor efficiency in spinning and difficulties in fiber collection.

Conventionally, nanofibers have been produced by the technique of electrospinning, as described in "Electrostatic Spinning of Acrylic Microfibers", P. K. Baumgarten, *Journal of Colloid and Interface Science*, Vol. 36, No. 1, May, 1971. According to the electrospinning process, an electric potential is applied to a drop of a polymer in solution hanging from a metal tube, for example a syringe needle, which results in elongation of the drop of the solution to form very fine fibers which are directed to a grounded collector. Fibers with diameters in the range of 0.05 to 1.1 micrometers (50 to 1100 nm) are reported. An example of a suitable electrospinning apparatus for forming the nanofiber-containing fabrics of the present invention is disclosed in U.S. Pat. No. 4,127,706, incorporated herein by reference.

The vast majority of investigations into nanofiber production reported in the prior art literature have been directed to formation of essentially hydrophilic polymer nanofibers, such as polyamide, polyurethane and the like. While some investigators have suggested that nanofibers could be produced from hydrophobic polymers, few actual examples of such hydrophobic nanofibers are disclosed in the literature. U.S. Pat. No. 4,127,706 discloses production of porous fluoropolymer fibrous sheet, suggesting the production of PTFE fibers with diameters in the range of 0.1 to 10 micrometers, but exemplifying only fibers with diameters of 0.5 micrometer and above.

SUMMARY OF THE INVENTION

One embodiment of the present invention is a nonwoven fabric comprising a support web and a fibrous barrier web, having a hydrohead of at least about 145 cm and a Frazier permeability of at least about 0.3 m$^3$/m$^2$-min.

Another embodiment of the present invention is a hydrophobic nonwoven fabric comprising at least one support web and a barrier web with fibers having diameters of less than 2.0 micrometers, a hydrohead of at least about 145 cm and a Frazier permeability of at least about 0.3 m$^3$/m$^2$-min.

Another embodiment of the present invention is a nonwoven fabric comprising a fibrous barrier web, said fabric having a hydrohead of at least about 145 cm and a Frazier permeability of at least about 0.3 m$^3$/m$^2$-min and having a relationship between barrier web basis weight, and fabric hydrohead and Frazier permeability described by the formula:

$$Bwt(g/m^2) \leq \frac{4000 \cdot c \cdot (1 - 2.3 \cdot c) \cdot \rho_f}{Frazier \cdot Hydrohead^{k(c)}},$$

wherein $\rho_f$ is the density of the barrier fibers, kg/m3, c is the solids volume fraction of the barrier web, $k(c)=3.58 \cdot c^2 - 1.32 \cdot c + 1.77$, Frazier is in units of m$^3$/m$^2$-min, and hydrohead is in units of centimeters of water column.

DETAILED DESCRIPTION OF THE INVENTION

Unless otherwise specified, references to fiber diameters herein are intended to be directed to the number average fiber diameter of the fibers.

Figure 1:
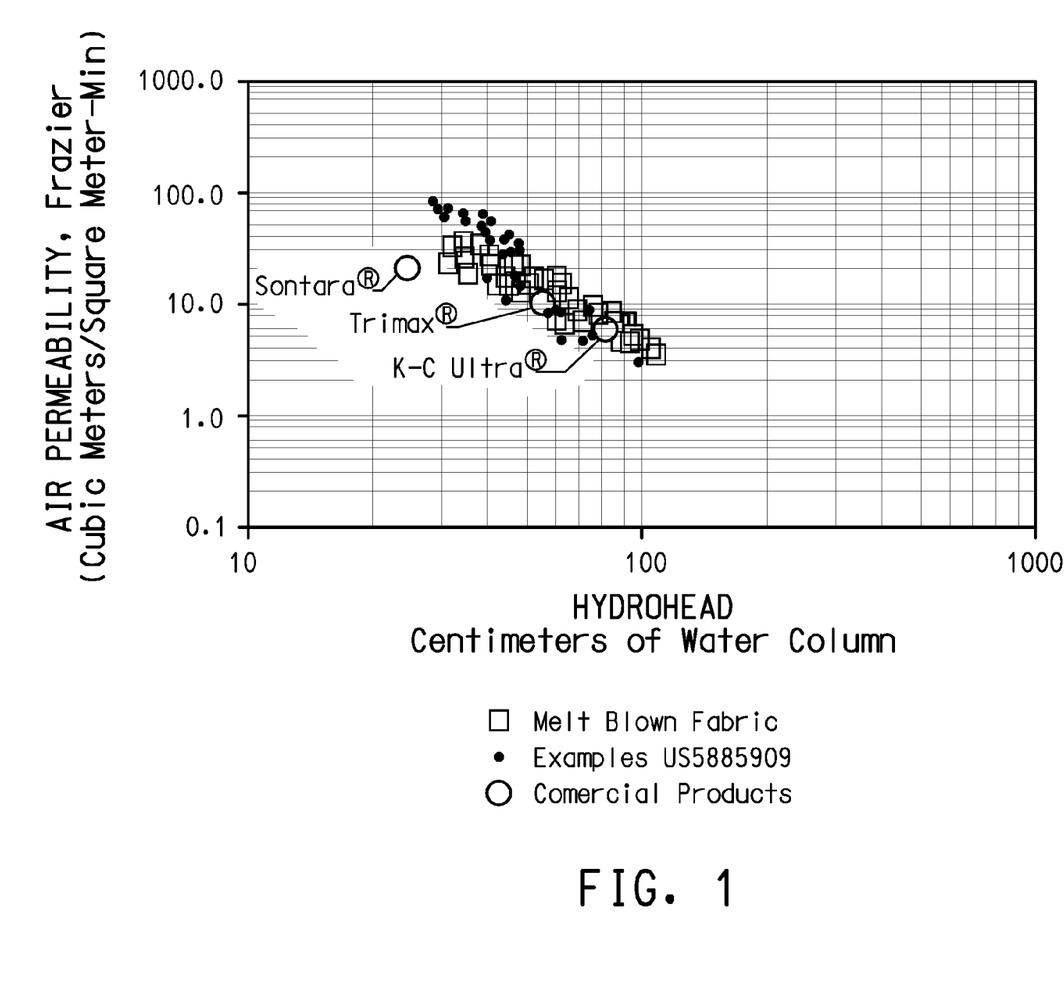
FIG. 1 is a log/log plot of barrier properties of various prior art fabrics.

FIG. 1 illustrates the inverse relationship between air permeability and hydrohead for three sets of data. The first set is taken from U.S. Pat. No. 5,585,909, the second presents data measured on samples of melt-blown nonwoven fabric, the third presents data measured on three commercial nonwoven products: K-C Ultra® unreinforced surgical gown, available from Kimberly Clark Health Care, Roswell, Ga.; Trimax® unreinforced surgical gown and DuPont Sontara® Optima® unreinforced surgical gown, both available from Allegiance Health Care, Mc Gaw Park, Ill.

It is of note in FIG. 1, that commercial nonwoven products have air permeabilities in the range of woven fabrics. By way of reference, a tightly woven polyester fabric (basis weight 95 g/m$^2$) used in the testing described above had a Frazier value of about 0.5 m$^3$/m$^2$-min, while, ASTM D737-96 lists the Frazier values for a sampling of several woven fabrics in the range of 2.5 to 66 m$^3$/m$^2$-min.

FIG. 1 shows that nonwoven barrier fabrics have a hydrohead typically lower than about 100 centimeters of water column. The forcing pressure difference, ΔP, across the fabric can be related to the equivalent capillary radius, R of the largest pore water will penetrate, using the Washburn equation:

$$\Delta P = -\frac{2\sigma}{R} Cos\theta. \quad \text{(Equation 1)}$$

Here σ is the surface tension of water (0.072 N/m) and θ is the wetting angle, i.e., the angle of intersection of the fluid surface with the solid surface. For ΔP in units of centimeters of water column and R in micrometers and assuming an ideally nonwetted surface (θ=180°), $$\Delta P(cmwc) = \frac{1468}{R(microns)}. \quad \text{(Equation 2)}$$

From which it is concluded that hydrohead lower than about 100 cmwc in FIG. 1 corresponds to largest pores of radius, R≥15 micrometers.

The Washburn relationship shows that to create better liquid barriers which can withstand higher fluid pressures, fabric pore size must be reduced. Better liquid barrier fabric would be of benefit in many applications including protective apparel. For example, in response to concern about contamination with blood-borne pathogens, ASTM F1670 specifies that an acceptable fabric must prevent penetration of synthetic blood ($\sigma$=0.042 N/m versus 0.072 N/m for water) at a pressure of 13800 N/m² (141 cmwc). From Equation 1, for a fabric to pass this test (wetting angle $\theta$=180°, the maximum fabric pore radius must be less than about 6 micrometers.

Microporous films with pores radii typically less than 1 micrometer satisfy this criterion. Such films can be effective liquid barriers, but they are very impermeable to air flow as well. Typical microporous film air permeabilities, e.g., in the range of Frazier<0.008 m³/m²-min, are too low to provide effective air exchange in a protective garment. This often leads to heat buildup and discomfort. In the extreme, it can even impair or limit work performance.

Fibrous porous media are inherently more permeable than microporous films and a good choice for protective fabrics, but the relationship of FIG. 1 shows, in general, that significant increases in barrier function resulting from reduced pore size will also significantly reduce air permeability.

To understand the requirements for a nonwoven fibrous fabric to have both high liquid barrier and high air permeability, it is useful to construct an analytical model of the fabric structure. Hydrohead as a measure of liquid barrier is related to pore size as discussed above, and pore size is determined by structural characteristics of the fabric, including fiber size and void fraction. Fabric air permeability is also determined by fundamental structural characteristics, including fiber size, void fraction and basis weight.

Pore Size:

The size of the pore space between fibers in a random fiber web, is proportional to fiber diameter, $D_f$, as a determinant of the number of fibers which can occupy a space. It is inversely proportional to the solids volume fraction, c, which is the ratio of web volume occupied by fibers to the total web volume (i.e., (1−void fraction)). For metal fiber filters, Goeminne, et al, ("The Geometrical and Filtration Characteristics of Metal Fiber Filters—A Comparative Study", *Filtration and Separation*, Vol. 11, No. 4, pp 350-355 (1974)) report that the maximum pore diameter, $D_p$ is described by:

$$Dp = \frac{D_f}{c}. \quad \text{(Equation 3)}$$

An independent analysis of the stochastic structure of ideal random fibrous webs for this work gives:

$$Dp = \frac{3 \cdot \pi \cdot D_f}{8 \cdot c}. \quad \text{(Equation 4)}$$

Equation 4 predicts slightly larger maximum pore size than Equation 3. Combining Equation 4 with Equation 2 provides a conservative estimate of random web hydrohead in terms of fiber size and solids fraction as:

$$\Delta P(cmwc) = \frac{2493 \cdot c}{D_f(\text{microns})}. \quad \text{(Equation 5)}$$

Equation 5 is used for the results below.

Air Permeability:

Davies has presented a careful and well attested correlation of flow rate, pressure drop, fiber size and solids fraction on pads made of a wide variety of fibrous materials. (Davies, C. N., "The Separation of Airborne Dust and Particles," *The Institution of Mechanical Engineers Proceedings* (*B*), Nos. 1-12, Vol 1B, p 185, 1952-53) In terms of definitions above, this correlation gives volumetric flow rate, Q, per unit flow area, A, as:

$$\frac{Q}{A} = \frac{\Delta P \cdot D_f^2}{h \cdot \eta \cdot f(c)}, \quad \text{(Equation 6)}$$

where, $$f(c) = 64 \cdot c^{1.5} \cdot (1 + 56 \cdot c^3). \quad \text{(Equation 7)}$$

Here $\Delta P$ is the pressure drop across the fibrous pad of thickness, h, and $\eta$ is the viscosity of the flowing fluid. The Davies correlation is valid for 0.006<c<0.3 when the flow around fibers in the medium is laminar.

The thickness of the fibrous medium is related to the basis weight (Bwt) of the medium, the fiber density, $\rho_f$, and the solids fraction as follows:

$$h = \frac{Bwt}{\rho_f \cdot c}. \quad \text{(Equation 8)}$$

Combining Equations 6 and 8, gives:

$$\frac{Q}{A} = \frac{\rho_f \cdot \Delta P \cdot D_f^2 \cdot c}{Bwt \cdot \eta \cdot f(c)}. \quad \text{(Equation 9)}$$

Taking hydrohead to be the forcing pressure, $\Delta P$, of Equation 5, the relationship between hydrohead and fiber size of Equation 5 can be combined with the above relationship between Q/A and fiber size to give $$\frac{Q}{A} = \frac{6.2 \times 10^6 \cdot \rho_f \cdot \Delta P \cdot c^3}{Bwt \cdot \eta \cdot Hydrohead^2 \cdot f(c)}. \quad \text{(Equation 10)}$$

Figure 2:
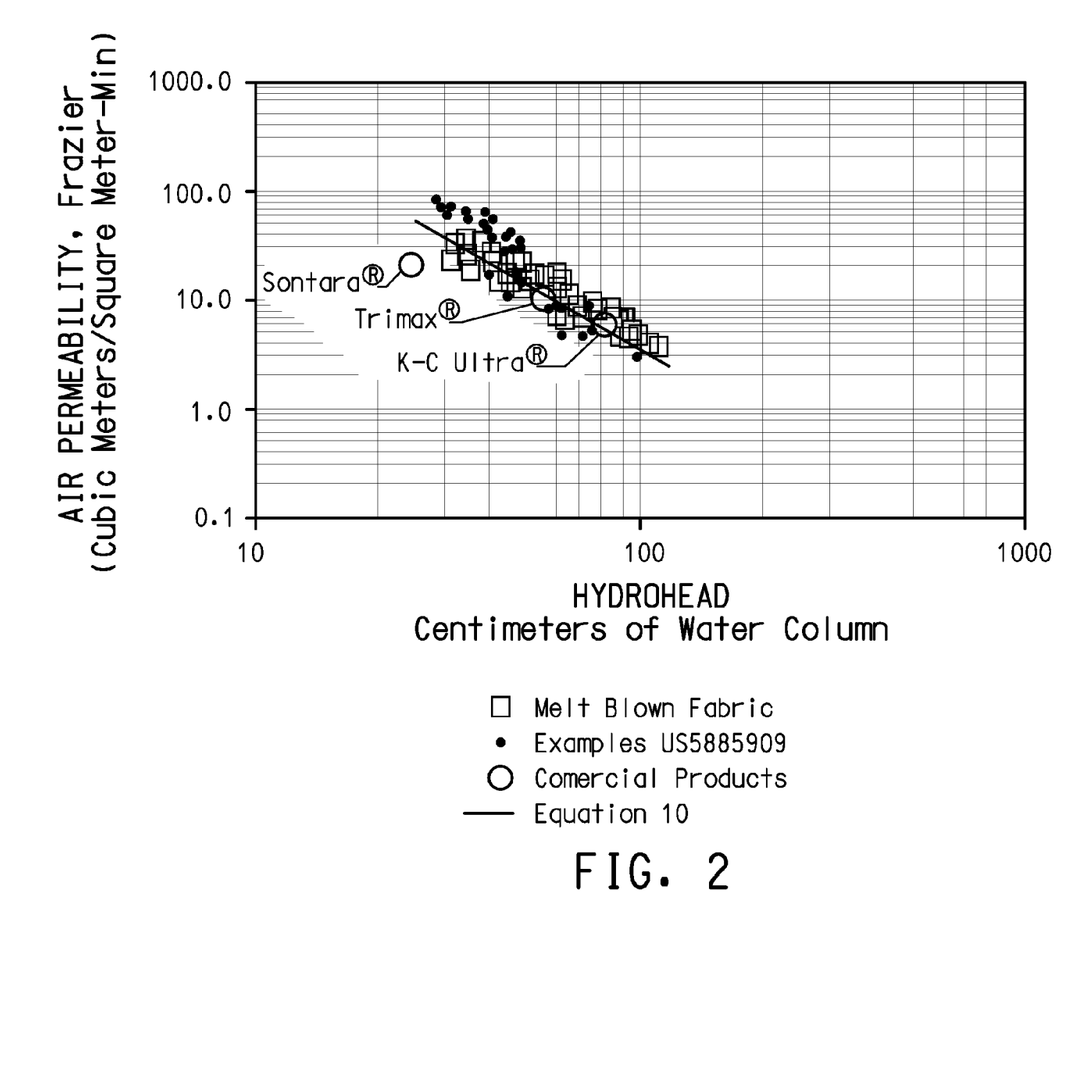
FIG. 2 is a reproduction of FIG. 1 with a plot of the line of Equation 10 laid thereon.

If the flow forcing pressure difference, $\Delta P$, of Equation 10 is set equal to 124.5 N/m², and consistent units are used, Q/A is calculated directly as Frazier in units of cubic meter per square meter per minute (m³/m²-min). FIG. 2 shows that for typical polypropylene fabrics, Bwt=34 grams/m², c=0.1, and $\rho_f$=920 kg/m³, the model of Equation 10 reasonably fits the data of FIG. 1 accounting for the general trend.

Two further refining effects must be taken into account. First, thermal bonding (which is almost always necessary in the production of nonwoven fabrics) at bond points which comprise a bonded area fraction, $f_{ba}$, will reduce Q/A by the factor $(1-f_{ba})$, hence, $$\frac{Q}{A} = \frac{\rho_f \cdot \Delta P \cdot D_f^2 \cdot c}{Bwt \cdot \eta \cdot f(c)} \cdot (1 - f_{ba}). \quad \text{(Equation 11)}$$

Second, for the fabrics with fiber sizes less than about 5 micrometers, air flow is known to "slip" past the fibers without encountering the full effects of viscous drag. The slip effect increases as fiber size decreases. The effect is to increase flow at a give pressure drop over that predicted by Equation 10. Chmielewski and Goren ("Aerolsol Filtration With Slip Flow", *Environmental Science and Technology*, Vol. 6, No. 13, p 1101, 1972) have presented a correction factor for the case of slip flow through fibrous fabrics. The correction factor, here defined as $S(c, N_{kn})$ varies with solids volume fraction, c, and with the Knudsen Number, $N_{kn}$, defined as $$N_{kn} = \frac{2.48 \cdot \lambda}{D_f}, \quad \text{(Equation 12)}$$

where $\lambda$ is the mean free path for collisions between air molecules. Here, $\lambda$ is taken to be 0.065 micrometers. For this work, the graphical presentation of Chmielewski and Goren was fit very well empirically with the function $$S(c, N_{kn}) = \frac{1 + \frac{(1.662 + 19.66 \cdot c - 47.027 \cdot c^2)}{N_{kn}}}{1 + .9489 \cdot N_{kn}}. \quad \text{(Equation 13)}$$

The slip correction is incorporated in the flow model which then becomes:

$$\frac{Q}{A} = \frac{\rho_f \cdot \Delta P \cdot D_f^2 \cdot c}{Bwt \cdot \eta \cdot f(c)} \cdot (1 - f_{ba}) \cdot S(c, N_{kn}). \quad \text{(Equation 14)}$$

As above, if the forcing pressure drop across the fabric, $\Delta P$, is 124.5 N/m² (12.7 mm of water column), and $\eta$ is the viscosity of air at room temperature, and if consistent units are used, then Q/A is the Frazier permeability, here denoted in units of m³/m²-min.

The present inventor has determined that the model for hydrohead, Equation 5, and the model for flow, Equation 14, can be used together to define the requirements for functionally superior liquid barrier fabrics. If the fabric is a multi-layer fabric, the model can be used for each layer to determine the properties of each, then the individual layer properties can be combined to determine composite sheet properties. For example, in a layered fabric, hydrohead is taken to be the maximum hydrohead of any layer in the fabric. Air permeability is obtained from the relationship:

$$\frac{1}{Frazier_{TotalFabric}} = \sum_{Layer=1}^{j} \frac{1}{Frazier_{Layer-j}}. \quad \text{(Equation 15)}$$

Models:
Model 1: Constant Basis Weight as Fiber Size is Decreased to Increase Liquid Barrier.

Figure 3:
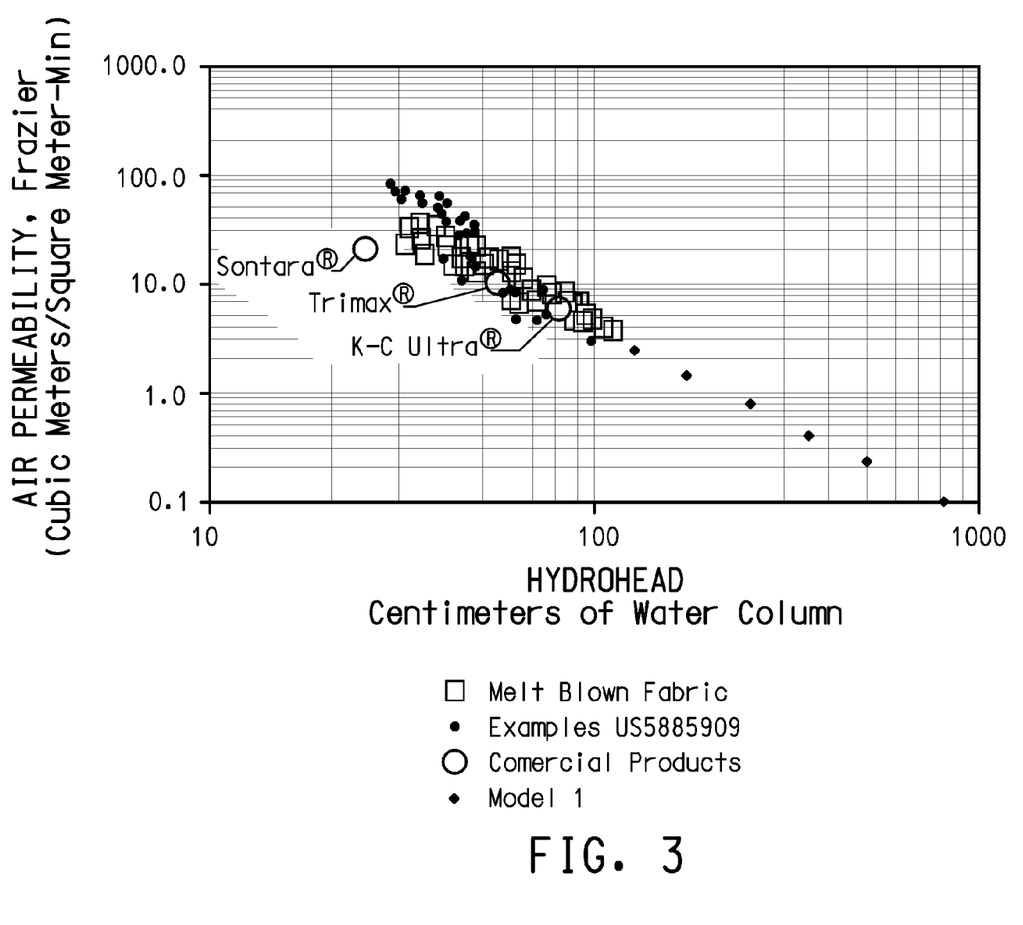
FIG. 3 is reproduction of FIG. 1 with a plot of data from Equation 14 wherein basis weight is maintained as a constant, and fiber size is reduced.

For the case of a polypropylene fabric where Bwt=33.9 g/m², $f_{ba}$=0, c=0.1, and $\rho_f$=920 kg/m³, the model provides the results of Table 1, and FIG. 3.

TABLE 1

| Fiber Diameter (micrometers) | Hydrohead (cmwc) | Frazier Permeability (m³/m²-min) |
|---|---|---|
| 2.0 | 125 | 2.58 |
| 1.5 | 166 | 1.54 |
| 1.0 | 249 | 0.75 |

TABLE 1-continued

| Fiber Diameter (micrometers) | Hydrohead (cmwc) | Frazier Permeability (m³/m²-min) |
|---|---|---|
| 0.7 | 356 | 0.41 |
| 0.5 | 499 | 0.23 |
| 0.3 | 831 | 0.10 |

The results of Model 1 illustrate the detrimental decrease of fabric permeability when liquid barrier is increased by decreasing fiber size alone, without a decrease in basis weight.

Model 2: Constant Air Permeability (Frazier) as Fiber Size is Decreased to Increase Liquid Barrier.

Figure 4:
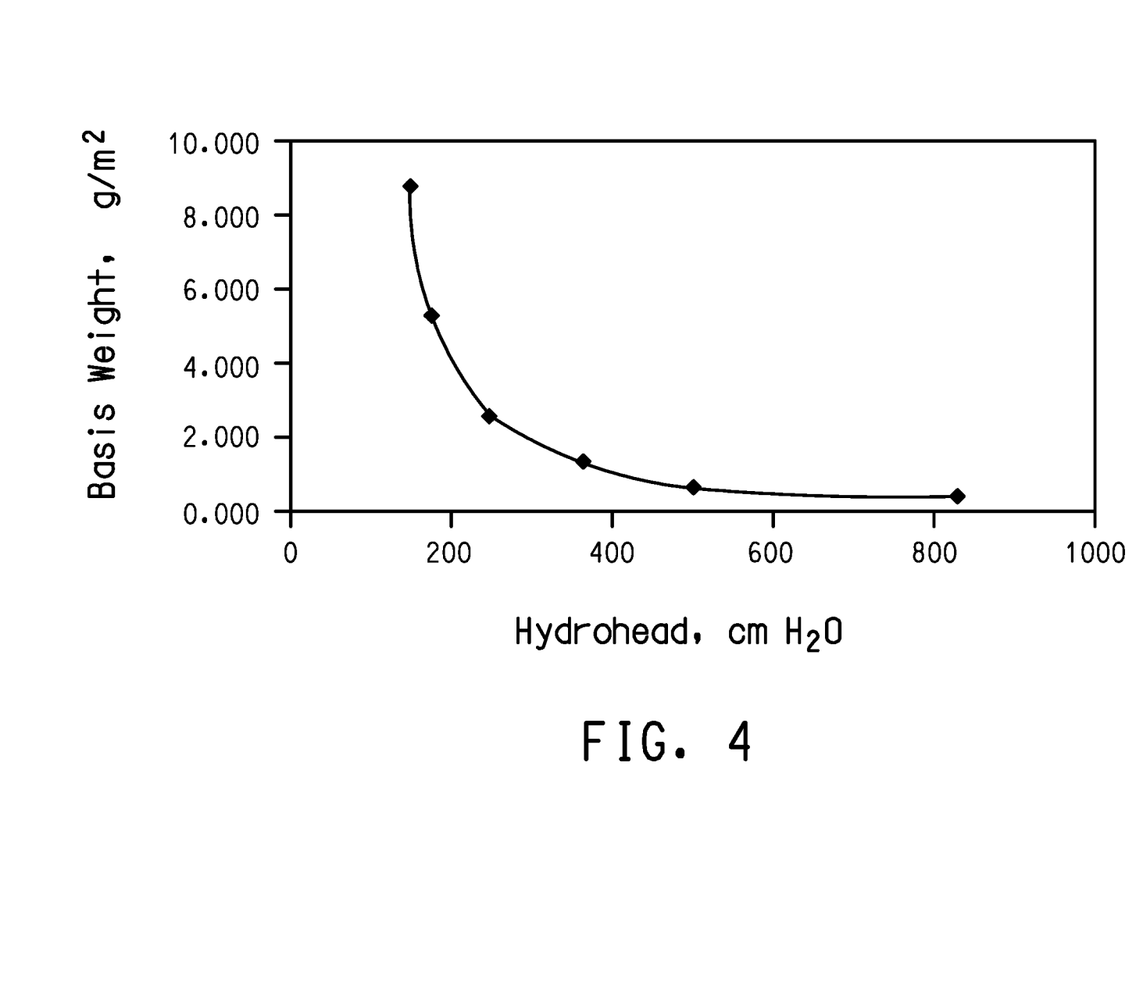
FIG. 4 is a plot of basis weight v. liquid barrier at constant air permeability (Frazier).
Figure 5:
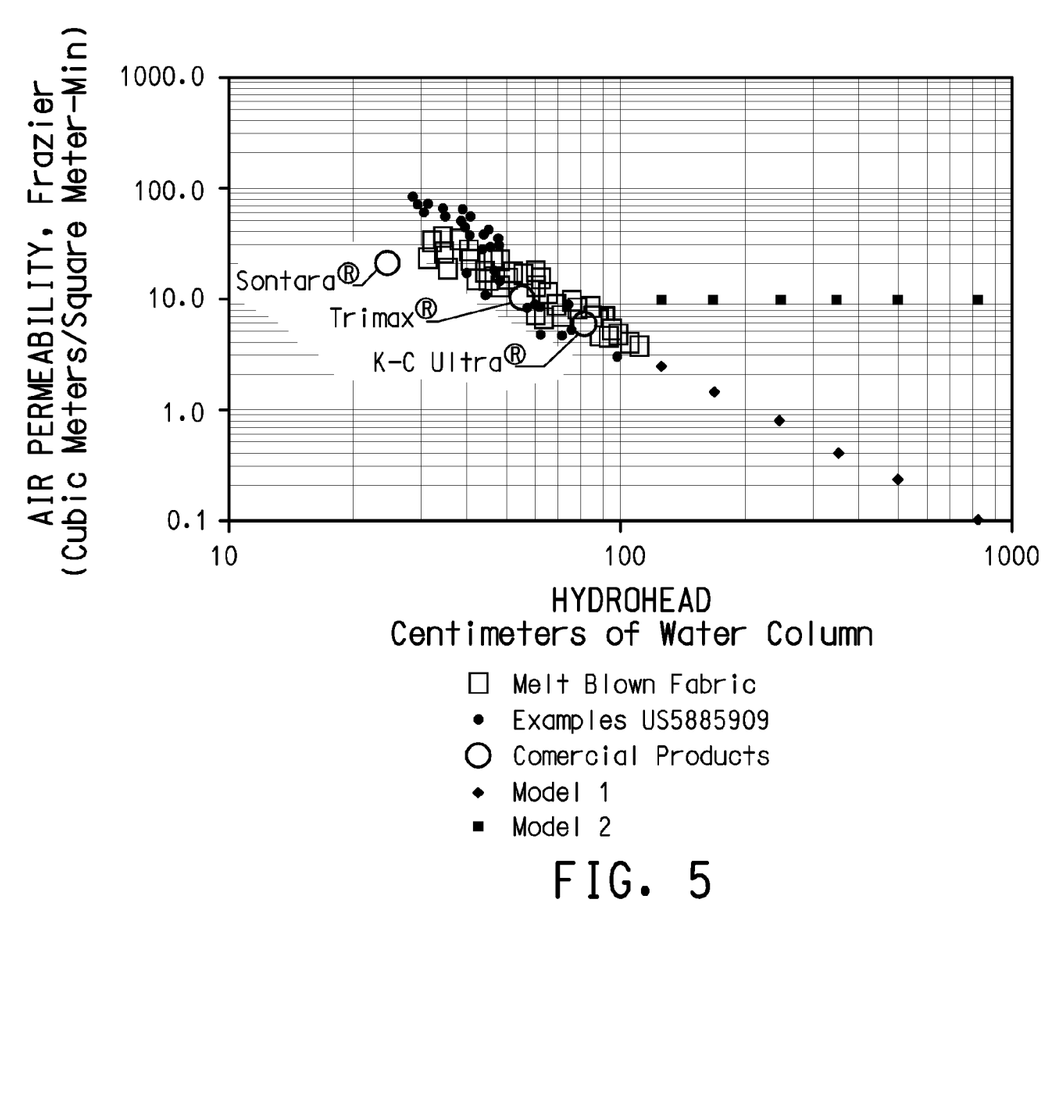
FIG. 5 is a reproduction of FIG. 3 with a plot of data from Equation 14 wherein air permeability (Frazier) is maintained as a constant, and fiber size is reduced.

For the case of a polypropylene fabric where Frazier=10 m³/m²-min, $f_{ba}$=0, c=0.1, and $\rho_f$=920 kg/m³, the model provides the results of Table 2, and FIGS. 4 and 5.

TABLE 2

| Hydrohead (cmwc) | Basis Weight (g/m²) |
|---|---|
| 125 | 8.761 |
| 166 | 5.213 |
| 249 | 2.553 |
| 356 | 1.386 |
| 499 | 0.788 |
| 831 | 0.339 |

From FIGS. 4 and 5, it is clearly seen that the basis weight of the barrier layer must be decreased dramatically to maintain air permeability as liquid barrier in terms of hydrohead is increased.

Figure 6:
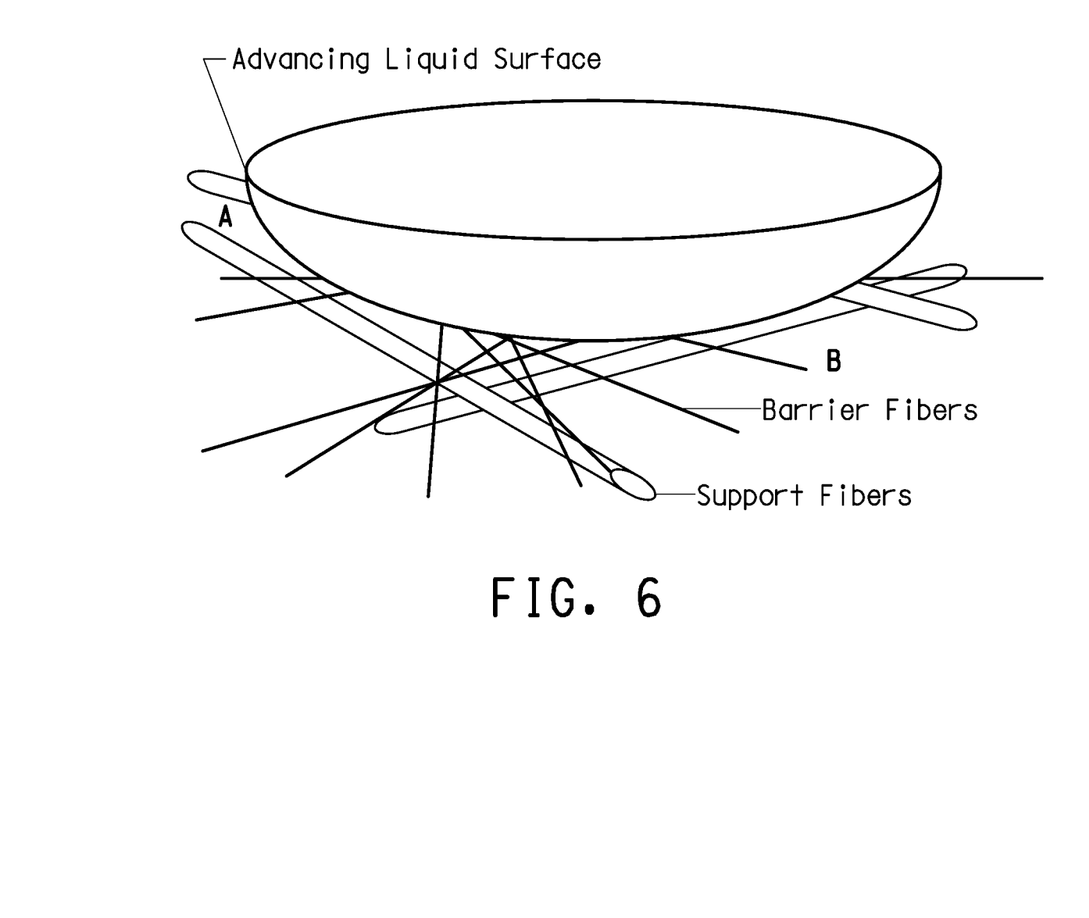
FIG. 6 is an illustration of the structure of the nonwoven fabrics of the present invention presenting a barrier to the advance of a liquid surface.

Problem of High Barrier and Thin Barrier Web:

In the extreme case of high permeability or high liquid barrier or both, the mechanical strength of the barrier layer can pose a practical limit the barrier level achieved. FIG. 6 shows a liquid interface advancing against a fibrous barrier layer. The barrier layer consists of a layer of small fibers with characteristically small pores supported by a layer of large fibers with characteristically larger pores. The pressure required to force a nonwetting fluid through the small pores of the barrier layer is given by Equation 5. This pressure force is distributed across all the small fibers of the barrier layer. Hence, the loading of a representative small fiber, e.g., Fiber AB, is readily obtained as a force per unit length. The span over which the small fiber must carry the pressure load is determined by the pore size of the support layer as given by Equation 4. If the span is too great, the tension in the small fibers can exceed the strength of the fibers, causing them to break.

In this case, the hydrohead is limited by a relationship between the strength of the barrier fiber, and the basis weight of the barrier fiber layer, which determine the strength of the barrier layer, and the pore size of the support layer which determines the force load on the barrier fibers. A relationship can be developed between the maximum force load a barrier fiber can sustain just before breaking and the force loading that the barrier fiber would have to sustain to achieve maximum hydrohead. If it is assumed that the barrier layer fiber loading and geometry are microscopic equivalents to the uniform loading of a macroscopic cable strung between two supports and if it is assumed that a small barrier fiber deflects a distance equivalent to one large support layer fiber diameter before it breaks, the analysis of this relationship as a cable problem gives:

$$\frac{Hydrohead_{act}}{Hydrohead_{max}} = 613 \cdot \frac{D_{fS}}{D_{fL}} \cdot \frac{GPD \cdot Bwt(g/m^2)}{\sqrt{1 + 0.0867 \cdot \frac{(D_{fL}/D_{fS})^2}{c^2}}},$$ (Equation 16)

(Higdon, A., Stiles, W. B., *Engineering Mechanics Statics and Dynamics*, Vector Edition, Prentice-Hall, 1962).

Here, Hydrohead$_{act}$ is the hydrohead actually achieved. Hydrohead$_{max}$ is the maximum hydrohead the barrier layer can achieve, given by Equation 5. $D_{fS}$ and $D_{fL}$ are the diameters of the small barrier layer fibers and the large support fibers respectively. GPD is the tensile strength of the barrier layer fibers in grams per denier. Bwt is the basis weight of the barrier layer. The solids volume fraction is c.

Model 3: Illustration of the Problem of Low Barrier Layer Strength when Barrier Layer Basis Weight is Reduced to Maintain Air Permeability If the barrier layer of Model 2 consisting of polypropylene ($\rho_f$=920 kg/m$^3$) fibers of diameter D$_{fS}$=0.6 micrometers (Frazier=10 m$^3$/m$^2$-min, c=0.1, GPD=1 gram per denier, and Bwt=1 g/m$^2$) is laminated to a support layer with fibers of diameter D$_{fL}$=12 micrometers, then Equation 16 gives:

$$\frac{Hydrohead_{act}}{Hydrohead_{max}} = 0.52.$$ (Equation 17)

The maximum potential hydrohead for the barrier layer as obtained from Equation 5 is 415 cmwc, but at a basis weight of 1 g/m$^2$, the layer is strong enough to withstand only about half of that pressure before collapsing. The maximum hydrohead could be realized by doubling the basis weight of the barrier layer, but doubling the basis weight would reduce the air permeability of the composite fabric by half. There would be an economic penalty as well for the higher basis weight.

Figure 7:
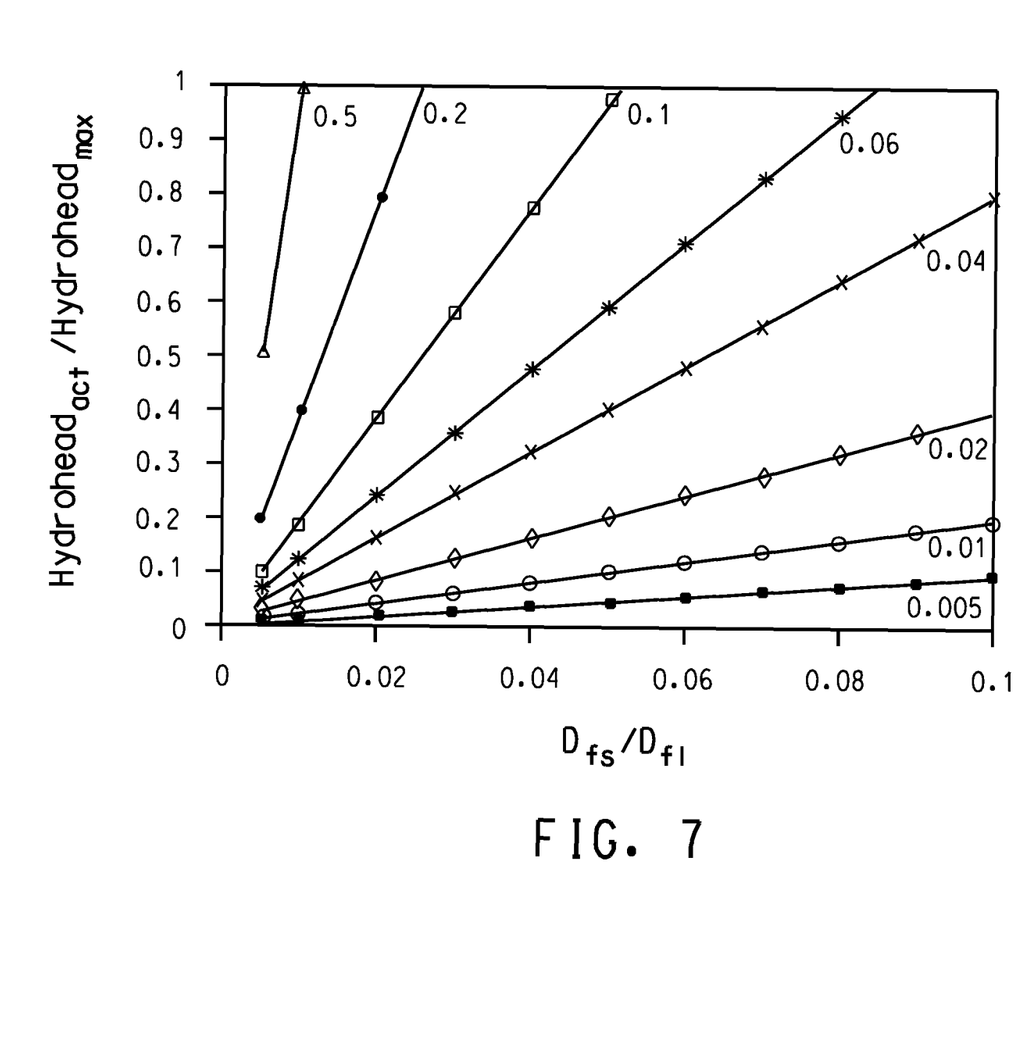
FIG. 7 is a graphical presentation illustrating the relationship of Equation 16 wherein achievable hydrohead as a fraction of potential hydrohead is dependent upon $D_{fS}/D_{fL}$ and GPD×Bwt.

An alternative solution is to reduce the pore size of the support layer by reducing the support layer fiber size. Per FIG. 7, the Hydrohead$_{act}$/Hydrohead$_{max}$ curve for GPD× Bwt=1, reaches unity when the ratio D$_{fS}$/D$_{fL}$=0.075. So the maximum hydrohead possible can be realized if the support layer fiber diameter is reduced to about 8 micrometers. If the basis weight of such a support layer is less than about 9 grams/m$^2$, per Equation 7, the Frazier air permeability, is still about 10 m$^3$/m$^2$-min.

The model relationships presented here permit the rational design of fabrics for various balances of barrier and air permeability. Clearly, the underlying physics allow only certain balances of properties to exist. Once a realizable balance is specified, choices can be made as to how to create a given balance.

For example, since permeability depends upon the square of fiber diameter, choosing the largest fiber size consistent with achieving a desired barrier might be preferred as a means of achieving the highest permeability. Hydrohead can be increased by calendering the fabric to increase solids fraction (Equation 5). The dependence of hydrohead and Frazier on solids fractions is such that calendering the barrier layer to increase the solids fraction will increase barrier more than it decreases Frazier. If smaller fiber size is selected for barrier as the product basis, basis weight can be adjusted within bounds to achieve the desired air permeability. Other such tradeoffs can be assessed based on economics and the practicalities of fabric processing.

The model presented is based on the geometry of a random fiber web made of rigid, straight, continuous fibers, of which a glass fiber mat is a good example. This is perhaps the simplest, most open and ideal web geometry. Certainly many deviations from this ideal exist in practice. A common deviation is due to non-random fiber deposition associated with fiber bunching or clumping. As discussed by Davies (cited above), the resulting structure acts as if it is made of fibers of an effective fiber size somewhat larger than the actual fiber size.

Changes in fiber properties which affect how fibers pack in three dimensions, such as fiber shape, stiffness, crimp, etc, will result in structural deviations from the ideal. Also, the fluid-fiber wetting characteristics reflected in surface tension, $\sigma$, and the wetting angle, $\theta$, may vary. In most cases this would reduce the maximum achievable hydrohead as per Equations 4 and 5. Hence, there can be other specific property balances and these are implicit in the scatter of the data in FIGS. 1 and 2 and the data set forth in Tables 4 and 5 below. In principle the model can be refined for specific cases. Nevertheless, the analysis of the ideal structure serves well as a benchmark and a guide.

The present invention is a nonwoven fabric comprising a support web and a barrier web, having a hydrohead of at least about 145 cm and a Frazier permeability of at least about 0.3 m$^3$/m$^2$-min. The nonwoven barrier sheet can be hydrophobic, said hydrophobicity being derived from either coating a hydrophilic sheet with a hydrophobic coating material, such as a fluorocarbon- or silicone-based coating material, or by forming the sheet from hydrophobic polymers or copolymers, such as polyolefins, including but not limited to those having repeating units derived from ethylene, propylene, butenes, hexenes, octenes, styrenes, 4-methylpentene-1 and combinations thereof, and partially fluorinated or perfluorinated polymers or copolymers, including but not limited to ethylene/tetrafluoroethylene (E/TFE), ethylene/chlorotrifluoroethylene, polyvinylidene fluoride (PVDF), fluorinated ethylene/propylene (FEP), a copolymer of tetrafluoroethylene and a perfluoro(alkyl vinyl ether) (PFA), and the like.

The diameter of the barrier web fibers is usually less than about 2 micrometers, more usually less than about 1 micrometer and can even be in the "nanofiber" range, having diameters of less than about 0.5 micrometer, wherein the diameter is the number average fiber size.

The fibers in the support webs for the barrier webs are usually less than 20 times, more usually less than 15 times and most usually less than 10 times the diameter of the corresponding barrier web fibers. For example, the support web fibers can have diameters greater than about 13 micrometers, which roughly corresponds to the diameter of conventional spunbond fibers, about 12 micrometers or less, which roughly corresponds to the diameter of micro-denier spunbond fibers, or about 5 micrometers or less, which roughly corresponds to the diameter of melt blown fibers.

The support web can be any fabric which is configured to provide suitable support to the very fine fiber web. Among suitable support webs are conventional spunbond and melt-blown webs, micro-denier spunbond webs such as disclosed in U.S. Pat. No. 5,885,909, and various combinations of such different conventional nonwoven webs with one or more of the very fine fiber webs.

It is also possible to provide a hydrophobic nonwoven sheet containing nanofibers according to the present invention by depositing a nonwoven web of conventional hydrophilic polymer nanofibers onto a collecting/supporting web and coating the web's nanofibers with a hydrophobic coating material, such as a fluorocarbon coating material. When the coating material is applied in an extremely thin layer, little if any change in the air permeability properties of the underlying web is caused, for example as described in co-pending U.S. provisional application No. 60/391,864, filed 26 Jun. 2002.

In order to minimize air flow resistance and maximize flexibility of the nonwoven fabrics of the invention, the support layer basis weight can be less than 17 g/m², or less than 14 g/m², or less than 11 g/m², or less than 7 g/m², or less than 3 g/m², or even less than 1 g/m².

The nonwoven fabrics of the present invention have hydroheads of at least about 145 cmwc and Fraziers of at least about 0.3 m³/m²-min, or at least about 1 m³/m²-min, or at least about 3 m³/m²-min, or at least about 5 m³/m²-min, or even at least about 10 m³/m²-min. The hydroheads of the inventive fabrics can be greater than or equal to 150 cmwc, greater than or equal to 200 cmwc, greater than or equal to 300 cmwc, or even greater than or equal to 400 cmwc.

The nonwoven fabrics of the present invention have maximum pore size between fibers, as measured by bubble point (ASTM E128), of less than about 23 micrometers, or less than about 20 micrometers, or less than about 15 micrometers, or even less than about 12 micrometers.

EXAMPLES

Sample fabrics were made by dissolving various polymers in suitable solvents which were then fed into an electrospinning apparatus, such as that described in U.S. Pat. No. 4,127,706, incorporated herein by reference. The fine fibers formed were deposited onto a melt blown fabric support layer to form a barrier layer of the fine fibers, and mechanical strength was imparted to the samples by sandwiching the fine fiber/melt blown layers between layers of spunbond polyester fibers, to form a four-layer laminate of spunbond/melt blown/fine fiber/spunbond configuration.

Fine fibers were spun from two different hydrophobic polymers: Kraton™ D1134x, a styrene-butadiene copolymer (specific gravity=0.94), available from Kraton™ Polymers of Houston, Tex.; and Kynar™ 761, a polyvinylidene fluoride polymer (specific gravity=1.76), available from Atofina Chemicals, Inc. of Philadelphia, Pa. Kraton™ fine fibers were spun from solutions of 9 wt. % polymer in a mixed solvent of 88/12 wt % tetrahydrofuran/dimethyl acetamide (THF/DMAC) and Kynar™ fine fibers were spun from solutions of 14-15 wt. % polymer in acetone.

A Sage™ Model 362 syringe pump by Orion was used to pump solution through a standard syringe with a blunt 27 gauge needle. High voltage was supplied to the needle by inserting the needle through an insulated aluminum foil strip connected to a Spellman SL300 negative high voltage power supply. To assure reliable syringe pump operation in a high voltage environment it was necessary to isolate the pump electrically and then to ground the power supply reference lead, the metal case, and the support jack of the syringe pump.

The deposition target was a brass disk 89 mm in diameter by 64 mm thick with a fully radiused edge. The disk was mounted on an electrically insulating stand, for example, make of Lexan®, such that it was suspended about 4 mm in front of the stand and connected via a screw through the stand to ground. A spunbond shroud (18 g/m² Remay polyester) covered the face of the disk and stand to keep fibers from accumulating on the back side of the disk. A 76 mm diameter circle was cut out of the shroud over the face of the disk to expose the target area. A circular portion of melt blown substrate was mounted in the target area. For Kraton™ spins, uniform deposition of fibers was aided by insulating the target area with a polymeric film.

In one Kynar™ case (Example 12), a 15×15 cm fabric was made by depositing fibers directly onto stainless steel cylinder 48 mm in diameter by 148 mm long. The melt blown layer was wrapped around the cylinder and the two layers were cut and peeled away to form the core laminate.

Fabric properties were measured on 25 mm diameter circular areas of each fabric.

Air permeability and Bubble Point were measured on a Porous Media, Inc. Capillary Flow Porometer, according to the principles of ASTM F778 and ASTM F316-03, respectively, and are reported as Frazier Permeability in units of m³/m²-min and pore size in micrometers, respectively.

Hydrohead measurements were run on an Aspull Mk III Hydrostatic Head tester per method AATC TM 127, modified by using aluminum plates and an O-ring seal to hold the small fabric samples. Hydrohead was recorded at the first water penetration and is reported in centimeters of water column (cmwc).

Fine fiber loading was measured gravimetrically by the mass difference of the sample before and after fine fiber deposition, and is reported as an average over the surface area of the sample (total grams fine fibers deposited/sample area).

CONTROL EXAMPLES

Three control examples were made of spunbond/melt blown/spunbond construction, wherein the spunbond layers were 18 g/m² polyester (polyethylene terephthalate) and the melt blown layers were 18 g/m² bicomponent 65 wt. % polyester/35 wt. % polyethylene fibers made according to the description of WO 01/09425 A1, incorporated herein by reference. The control fabrics were prepared in the same way as the exemplary fabrics, except that no fine fiber layer was deposited.

TABLE 3

| Control Example # | Frazier (m³/m²-min) | Hydrohead (cmwc) |
|---|---|---|
| 1 | 31.4 | 29 |
| 2 | 6.7 | 57 |
| 3 | 7.7 | 56 |

A number of electrospinning runs were conducted in order to determine the most effective combination of polymer, solvents, and concentrations, as well as uniform deposition and handling techniques, to make the fine fiber barrier layers of the present invention. Data from the best combination of electrospinning parameters and collection techniques determined is set forth below.

Examples 1-9

Kraton™ D1133x copolymer was dissolved in a mixed solvent of 88 wt. % tetrahydrofuran/12 wt. % dimethyl acetamide at a polymer concentration of 9 wt. %, and electrospun at −18 KV at a rate of 0.5 ml/hr. Fine fibers were deposited onto samples of 18 g/m² bicomponent melt blown fabric described in the Control Examples at a collection distance of approximately 22 cm. The fine fiber layer was then covered with a layer of spunbonded polyester, removed from the sample target. The layer of melt blown collection fabric was also covered with a layer of spunbonded polyester and all four layers were consolidated into a laminate. The barrier properties of the Examples were measured and are reported below in Table 4.

The fine fibers collected were measured by scanning electron microscopy and found to have diameters in a general range of between about 0.1 to 1.8 micrometers, with the average fiber diameters believed to be less than about 1 micrometer.

TABLE 4

| Example # | Fiber load (g/m²) | Frazier (m³/m²-min) | Hydrohead (cmwc) | Bubblepoint (micrometers) |
|---|---|---|---|---|
| 1 | 5* | 0.4 | 222 | — |
| 2 | 2.5 | 1.6 | 79 | — |
| 3 | 11 | .24 | 37 | — |
| 4 | 4.8 | 0.6 | 86 | — |
| 5 | 1.5 | 3.2 | 26 | — |
| 6 | 2.6 | 1.0 | 92 | — |
| 7 | 6.0 | 0.7 | 118 | — |
| 8 | 1.5 | 3.8 | 105 | — |
| 9 | 12.8 | 0.3 | 128 | 21.6 |

*Estimate based on measured average and visual assessment of mass distribution.

In some cases the fine fibers were observed to shrink and crack upon drying. While the reasons for the data inconsistencies are not fully understood, it is believed that the relative humidity of the air during sample formation and collection drastically affects the spinning process and ultimately the barrier properties of the styrene-butadiene/THF/DMAC system, which makes it difficult to obtain uniform fiber deposition across the surface of the collection webs and barrier properties.

Examples 10-19

Kynar™ polymer was dissolved in acetone solvent at a polymer concentration of 15 wt. %, and electrospun at −20 KV at a rate of 5 ml/hr. Fine fibers were deposited onto samples of 18 g/m² bicomponent melt blown fabric described in the Control Examples at a collection distances of approximately 22-30 cm. The fine fiber layer was then covered with a layer of spunbonded polyester, removed from the sample target. The layer of melt blown collection fabric was also covered with a layer of spunbonded polyester and all four layers were consolidated into a laminate. The barrier properties of the Examples were measured and are reported below in Table 5.

The fine fibers collected were measured by scanning electron microscopy and found to have diameters in a general range of between about 0.14 to 2.8 micrometers, with the average fiber diameters believed to be less than about 1 micrometer.

TABLE 5

| Example # | Fiber load (g/m²) | Frazier (m³/m²-min) | Hydrohead (cmwc) | Bubblepoint (micrometers) |
|---|---|---|---|---|
| 10 | 13.6 | 11.2 | 131 | 11.3 |
| 11 | 22 | 3.1 | 115 | 10.9 |
| 12 | 16.5 | 1.0 | 278 | 10.7 |
| 13 | " | 2.1 | 347 | — |
| 14 | 51.1 | 0.7 | 399 | 9.4 |
| 15 | 22.7 | 1.6 | 345 | 11.8 |
| 16 | 26 | 1.0 | 368 | 8.0 |
| 17 | 15.4 | 1.5 | 322 | 8.7 |
| 18 | 23.9 | 0.7 | 332 | 4.3 |
| 19 | 20.0 | 0.8 | 279 | 5.8 |

Example 13 was a portion of the fabric sample of Example 12 which was calendered using a metal roll on a metal plate with a linear pressure estimated to be about 2-4 kg/cm.

Overall, the barrier fabrics containing the Kynar™ fine fibers exhibited much greater hydrohead values than those of either the Control Samples or Examples 1-9. It is believed that the more hydrophobic nature of the polyvinyl idene fluoride polymer in Examples 10-19, relative to the styrene-butadiene polymer of Examples 1-9, is a major reason for the improved hydrohead values. However, those of skill in the art will recognize that the hydrohead of the styrene-butadiene polymer fabrics of Examples 1-9 could be enhanced by treatment with a water-repellant chemical finish, such as a fluorochemical finish, without appreciable detriment to the Frazier permeability of the fabrics.

Further, it is important to note that in almost all cases, the hydrohead measurements of the fine fiber-containing exemplary fabrics of the present invention exceed those of the Control Examples, which are essentially spunbond/melt blown/spunbond fabric construction. This demonstrates that the presence of a fine fiber layer, especially wherein the fine fibers comprise fibers of less than about 2 micrometers in diameter, or even less than about 1 micron in diameter, can greatly enhance liquid barrier properties of a fabric.

The laminate fabric configurations, Fine Fiber barrier layer/spunbond support layer (FF/SB) and spunbond support layer/Fine Fiber barrier layer/spunbond support layer (SB/FF/SB) are viable configurations for achieving higher barrier with air permeability below about Frazier=1 m³/m²-min. Typical spunbond fiber diameter size is 10 micrometers and above.

Suitable support layers must have pore sizes scaled to the mechanical strength of the barrier layer. The weaker the barrier layer, the smaller the support layer pore size must be for adequate support. Smaller pores sizes, in turn, require smaller fiber diameter sizes. Hence, as barrier layer basis weight is reduced to facilitate high air permeability, suitable support layers must have fiber diameter sizes smaller than typical spunbond fiber sizes.

Such smaller fibers could be micro-denier spunbond (mSB), as discussed in U.S. Pat. No. 5,885,909, e.g., $6<D_f<10$ micrometers which are strong enough to meet the mechanical strength requirements for the fabric as a whole. Micro-denier spunbond support would give rise to two fabric configurations: FF/mSB and mSB/FF/mSB.

Non-self-supporting support layers with fiber diameters in the range of $1<D_f<10$ micrometers can be made by the melt blowing process. Typically these fibers are not strong (0.3<GPD<0.6). They are used to provide barrier properties with a support layer of spunbond fibers to provide strength. If melt blown fibers are used to support the Fine Fiber barrier layer, the melt blown fiber layer still requires a support layer to maintain over all fabric mechanical strength. A spunbond fiber layer is well suited to be the support layer.

This gives rise to the laminate fabric configurations: FF/MB/SB, SB/MB/FF/MB/SB, FF/MB/mSB and mSB/MB/FF/MB/mSB.

There can be asymmetrical combinations of these layer types, e.g., SB/FF/MB/SB, which could have asymmetrical barrier performance, which might provide unusual but useful function to fabrics of such constructions. For example, if the liquid challenge is from the SB/FF side, the barrier will be high and equal to the maximum barrier capability of the FF layer. If the liquid challenge is from the SB/MB side, the spunbond layer will not provide adequate support for the FF layer which will break at some hydrohead lower than FF layer capability.

I claim:

1. A nonwoven fabric comprising at least one support web of fibers and a hydrophobic barrier web with a basis weight from 5 g/m² to 51.1 g/m² and comprising fibers having a number average fiber diameter of less than 1.0 micrometer, said nonwoven fabric having a hydrohead of between 145 cm and 400 cm and a Frazier permeability of between 0.3 m³/m²-min and 11.2 m³/m²-min, wherein barrier web comprises fibers of hydrophobic polymer or copolymer and the polymer or copolymer are both selected from the group consisting of a polyolefin, a partially fluorinated and perfluorinated polymer or copolymer, and the fibers of the support web have diameters of less than 20 times the barrier web fiber diameters.

2. The nonwoven fabric of claim 1, wherein said barrier web fibers have diameters of less than 0.5 micrometer.

3. The nonwoven fabric of claim 1, wherein said polyolefin hydrophobic polymer or copolymer has repeating units derived from ethylene, propylene, butenes, hexenes, octenes, styrenes, 4-methylpentene-1 and combinations thereof.

4. The nonwoven fabric of claim 1, wherein the barrier web has a maximum pore size between fibers of no more than about 23 micrometers.

5. The nonwoven fabric of claim 1, wherein the barrier web has a solids fraction of no less than about 0.03.

6. The nonwoven barrier fabric of claim 1 having a relationship between barrier web basis weight, and fabric hydrohead and Frazier permeability described by the formula:

$$Bwt(g/m^2) \leq \frac{4000 \cdot c \cdot (1 - 2.3 \cdot c) \cdot \rho_f}{Frazier \cdot Hydrohead^{k(c)}},$$

wherein $\rho_f$ is the density of the barrier fibers, kg/m³ c is the solids volume fraction of the barrier web, $k(c)=3.58 \cdot c^2 - 1.32 \cdot c + 1.77$, Frazier is in units of m³/m²-min, and Hydrohead is in units of centimeters of water column.

7. A nonwoven fabric according to one of claim 1 or 6, comprising a structure of FF/mSB, wherein FF is a barrier web.

8. A nonwoven fabric according to one of claim 1 or 6, comprising a structure of FF/SB, wherein FF is a barrier web.

9. A nonwoven fabric according to one of claim 1 or 6, comprising a structure of mSB/FF/mSB, wherein FF is a barrier web.

10. A nonwoven fabric according to one of claim 1 or 6, comprising a structure of FF/MB/SB, wherein FF is a barrier web.

11. A nonwoven fabric according to one of claim 1 or 6, comprising a structure of SB/MB/FF/MB/SB, wherein FF is a barrier web.

12. A nonwoven fabric according to one of claim 1 or 6, comprising a structure of FF/MB/mSB, wherein FF is a barrier web.

13. A nonwoven fabric according to one of claim 1 or 6, comprising a structure of mSB/MB/FF/MB/mSB, wherein FF is a barrier web.

14. A nonwoven fabric according to one of claim 1 or 6, comprising a structure of SB/MB/FF/SB, wherein FF is a barrier web.

15. The nonwoven fabric of claim 1, wherein said support web fibers have diameters less than about 13 micrometers.

* * * * *